United States Patent [19]

O'Rand et al.

[11] Patent Number: 5,175,148

[45] Date of Patent: Dec. 29, 1992

[54] SPERM ANTIGEN CORRESPONDING TO A SPERM AUTOANTIGENIC EPITOPE AND METHODS OF USING THE SAME

[75] Inventors: Michael G. O'Rand; Esther E. Widgren, both of Chapel Hill, N.C.

[73] Assignee: The University of North Carolina at Chapel Hill, Chapel Hill, N.C.

[21] Appl. No.: 441,097

[22] Filed: Nov. 24, 1989

[51] Int. Cl.$^5$ .................. A61K 37/02; C07K 7/06; G01N 33/566

[52] U.S. Cl. .................. 514/15; 424/88; 436/501; 436/543; 514/2; 514/14; 514/841; 530/326; 530/327; 530/328

[58] Field of Search ............ 530/326, 327, 328; 514/2, 14, 15; 436/543, 547; 424/88

[56] References Cited

U.S. PATENT DOCUMENTS 4,857,634  8/1989  Minor et al. .................. 530/324

OTHER PUBLICATIONS

O'Rand, M. and Porter, J., "Isolation of a Sperm Membrane Sialoglycoprotein Autoantigen from Rabbit Testes," *The Journal of Immunology* 122, No. 4, 1248 (1979).

O'Rand, M. and Porter, J. "Isolation of Rabbit Sperm Immobilizing Autoantigens from Immunoabsorbent Chromatography," *Biol. Reprod. Supplement* 18, No. 1, 119 (1978).

O'Rand, M. and Porter, J. "Purification of Rabbit Sperm Autoantigens by Preparative SDS Gel Electrophoresis: Amino Acid and Carbohydrate Content of RSA-1," *Biology of Reproduction* 27, 713 (1982).

O'Rand, M. et al., "Monoclonal Antibodies to Rabbit Sperm Autoantigens, I. Inhibition of In Vitro Fertilization and Localization on the Egg," *Biology of Reproduction* 30, 721 (1984).

O'Rand, M. and Irons, G., "Monoclonal Antibodies to Rabbit Sperm Autoantigens, II, Inhibition of Human Sperm Penetration of Zona-Free Hamster Eggs," *Biology of Reproduction* 30, 731 (1984).

O'Rand, M. et al., "Characterization of the Rabbit Sperm Membrane Autoantigen, RSA, as a Lectin-like Zona Binding Protein," *Developmental Biology* 129, 231 (1988).

Welch, J. et al., "Isolation of a Testis Specific cDNA with Alloantiserum to a Rabbit Sperm Membrane Autoantigen, RSA-1," *J. Cell Bilogy* 103, 482a (1986).

*Primary Examiner*—Sam Rosen
*Attorney, Agent, or Firm*—Bell, Seltzer, Park & Gibson

[57] ABSTRACT

Disclosed is a synthetic peptide, useful as an immunocontraceptive agent and for the diagnosis of autoimmune infertility, which corresponds to an autoantigenic epitope of Rabbit Sperm Membrane Autoantigen (RSA). The synthetic peptide is selected from the group consisting of the decapeptide NH$_2$-pro-gly-gly-gly-thr-leu-pro-pro-ser-gly-COOH and the antigenic equivalents thereof.

Also disclosed is a method of diagnosing autoimmune infertility in a human subject. The method comprises the step of, first, contacting an immune sera sample from the subject with an antigen, the antigen selected from the group consisting of RSA, other proteins which bind selection antibodies which bind to RSA, and derivatives thereof which bind selection antibodies which bind to RSA. The next step is to detect the presence of antibodies from the immune sera sample bound to the antigen, the presence of antibodies bound to the antigen suggesting the subject is afflicted with autoimmune infertility. A preferred group of antigens is the decapeptide NH$_2$-pro-gly-gly-gly-thr-leu-pro-pro-ser-gly-COOH and the antigenic equivalents thereof.

14 Claims, 4 Drawing Sheets

KALLIKREIN DIGEST OF
14 kd RSA

5,175,148

SPERM ANTIGEN CORRESPONDING TO A SPERM AUTOANTIGENIC EPITOPE AND METHODS OF USING THE SAME

FIELD OF THE INVENTION

The present invention relates to antigens which correspond to an autoantigenic epitope on sperm, therapeutic methods employing these antigens, and diagnostic methods employing these and other antigens.

BACKGROUND OF THE INVENTION

Autoantigens are tissue components of an organism to which that organism directs an immune response. The condition which results from such a self-directed immune response is known as autoimmunity (or "autoallergy"). Proteins in or on sperm are known to be potent autoantigens, and autoimmunity to such proteins is believed a significant cause of infertility.

The rabbit sperm membrane autoantigen, RSA, is an essential sperm antigen which functions in fertilization. As a family of autoantigens which was originally isolated from rabbit epididymal sperm membranes and testis membrane pellets using a rabbit anti-rabbit sperm autoantibody immunoaffinity column, M. O'Rand and J. Porter, 122 *J. Immunol.* 1248 (1979), RSA consists of four low molecular weight protein staining bands of 14, 16, 17 and 18,000 apparent molecular weight. M. O'Rand et al., 129 *Dev. Biol.* 231 (1988). The ability to block the cytotoxic activity (sperm immobilization) of autoantiserum on live rabbit spermatozoa in the presence of complement is characteristic of the RSA family, M. O'Rand and J. Porter, 122 *J. Immunol.* 1248 (1979), as is its ability to form higher molecular weight aggregates, some of which are resistant to boiling, reduction and SDS treatment, M. O'Rand et al., 129 *Dev. Biol.* 231 (1988). RSA functions as a sperm lectin which binds the spermatozoon to the zona pellucida with high affinity (dissociation constant $5.6 \times 10^{-13}$M) and which can prevent spermatozoa from binding to zona-intact eggs, M. O'Rand et al. Id. Moreover, specific monoclonal and polyclonal anti-RSA antisera inhibit fertilization both in vivo and in vitro. M. O'Rand, 25 *Biol. Reprod.* 611 (1981); M.O'Rand et al., 30 *Biol. Reprod.* 721 (1984); M. O'Rand and G. Irons, 30 *Biol. Reprod.* 731 (1984).

The present invention arose from our continuing efforts to understand the molecular biology of sperm autoantigens. Specific objects of the present invention are to provide methods of diagnosing immune infertility in human subjects and to provide synthetic peptides useful for both diagnosing immune infertility and as immunocontraceptive agents.

SUMMARY OF THE INVENTION

A first aspect of the present invention is a synthetic peptide, useful as an immunocontraceptive agent and for the diagnosis of autoimmune infertility, which corresponds to an autoantigenic epitope of RSA. The synthetic pepetide is selected from the group consisting of the decapeptide NH$_2$-pro-gly-gly-gly-thr-leu-pro-pro-ser-gly-COOH and the antigenic equivalents thereof. The antigenic equivalents are selected from the group consisting of: (a) modified decapeptides comprising the aforesaid decapeptide modified by the inclusion of one or more changes to the amino acid sequence thereof; and (b) longer peptides which incorporate the sequence of the decapeptide or the modified decapeptide and which have (i) up to four extra amino acid residues attached to the C-terminal end thereof, (ii) up to four extra amino acid residues attached to the N-terminal end thereof, or (iii) up to four extra amino acid residues attached to the C-terminal end thereof and up to four extra amino acid residues attached to the N-terminal end thereof.

A second aspect of the present invention is based upon the finding that the aforesaid synthetic peptide binds autoimmune antisera from infertile humans. Thus, disclosed herein is method of diagnosing autoimmune infertility in a human subject. The method comprises the step of, first, contacting an immune sera sample from the subject with an antigen, the antigen selected from the group consisting of Rabbit Sperm Membrane Autoantigen (RSA), other proteins which bind selection antibodies which bind to RSA, and derivatives thereof which bind selection antibodies which bind to RSA. The next step is to detect the presence of antibodies from the immune sera sample bound to the antigen, the presence of antibodies bound to the antigen suggesting the subject is afflicted with autoimmune infertility.

The foregoing and other objects and aspects of the present invention are explained in detail in the text and figures which follow.

DETAILED DESCRIPTION OF THE INVENTION

Figure 1:
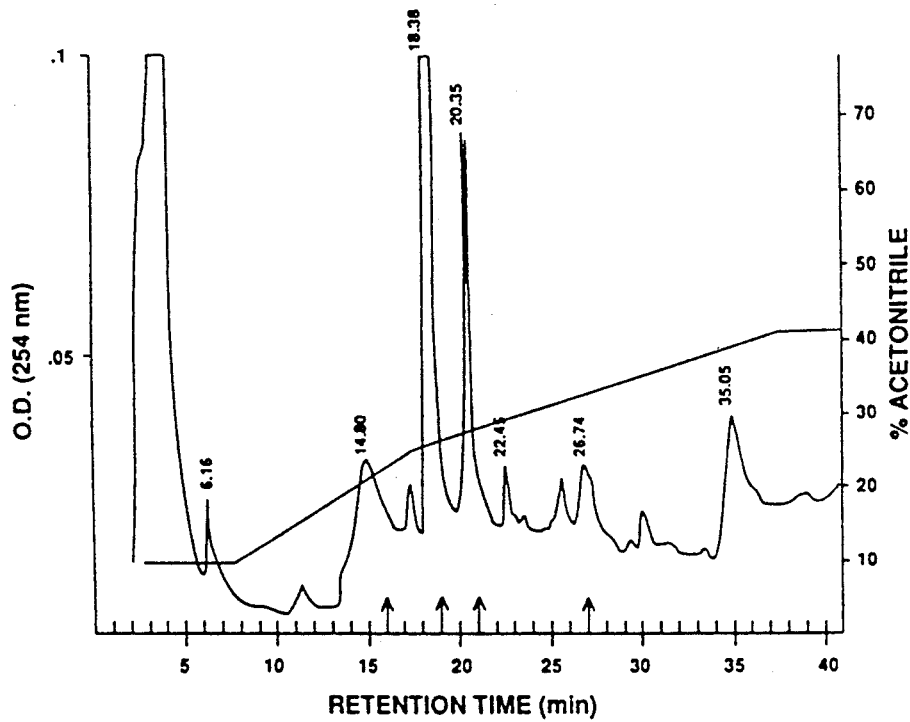
FIG. 1 shows the HPLC profile of a kallikrein digest of 14 kd RSA. The arrows indicate the four peaks which were selected for analysis. The sequence was obtained from fraction 21 (see Example 3). Retention times and the acetonitrile gradient are indicated.

The following abbreviations are used for the amino acid radicals herein, in accordance with standard usage:

| | |
|---|---|
| Ala = Alanine | Leu = Leucine |
| Arg = Arginine | Lys = Lysine |
| Asn = Asparagine | Met = Methionine |
| Asp = Aspartic acid | Phe = Phenylalanine |
| Cys = Cysteine | Pro = Proline |
| Gln = Glutamine | Ser = Serine |
| Glu = Glutamic acid | Thr = Threonine |
| Gly = Glycine | Trp = Tryptophan |
| His = Histidine | Tyr = Tyrosine |
| Ile = Isoleucine | Val = Valine |

The term "antigenic equivalents," as used herein, refers to proteins or peptides which bind to an antibody which binds to the protein or peptide with which equivalency is sought to be established. Antibodies which are used to select such antigenic equivalents are referred to as "selection antibodies" herein.

The most preferred synthetic peptide for carrying out the present invention is a decapeptide of the formula NH$_2$-pro-gly-gly-gly-thr-leu-pro-pro-ser-gly-COOH. This decapeptide was synthesized following the identification a consensus sequence from digests of RSA, this sequence having the formula, from the N terminal to C terminal thereof, of -ser-pro-gly-gly-gly-thr-leu-pro-pro-ser-gly-gly-trp-trp-ser-. Thus, exemplary of one longer peptide which may be used in carrying out the present invention is a peptide consisting of the consensus sequence, or NH$_2$-ser-pro-gly-gly-gly-thr-leu-pro-pro-ser-gly-gly-trp-trp-ser-COOH. In general, longer peptides preferably include the sequence of the decapeptide, (the sequence, from N terminal to C terminal thereof, of -pro-gly-gly-gly-thr-leu-pro-pro-ser-gly-). More preferably, longer peptides include the sequence of the consensus sequence. Longer peptides provide the antigenic sequence in an exposed position on the molecule, and not buried in the interior of the molecule where it would be unavailable for a binding event. Longer peptides which add not more than four additional amino acids to either the N terminal or C terminal of the decapeptide are preferred because sequences of such length are generally insufficient to provide an additional epitope on the longer peptide which might be detrimental to the activity of the synthetic peptide.

One or more amino acids of a synthetic peptide sequence may be replaced by one or more other amino acids which does not affect the antigenicity of that sequence. Such changes can be guided by known similarities between amino acids in physical features such as charge density, hydrophobicity/hydrophilicity, size and configuration. For example, Thr may be replaced by Ser and vice versa. Asp may be replaced by Glu and vice versa. and Leu may be replaced by Ile and vice versa. Once made. changes can be routinely screened to determine their effects on antigenicity with antibodies which bind to the decapeptide.

Antigenic equivalents may be formed by modifying reactive groups within a natural sequence or modifying the N-terminal amino and/or C-terminal carboxyl group. Such equivalents include salts formed with acids and/or bases, particularly physiologically acceptable inorganic and organic acids and bases. Other equivalents include modified carboxyl and/or amino groups on the synthetic peptide to produce esters or amides, or amino acid protecting groups such as N-t-butoxycarbonyl. Preferred modifications are those which provide a more stable, active peptide which will be less prone to enzymatic degradation in vivo.

Because the synthetic peptides of the present invention correspond to an autoantigenic epitope involved in autoimmune infertility, they can be used as an immunocontraceptive agent. Thus, the present invention provides an immunocontraceptive method comprising administering an animal subject a synthetic peptide as described above in an amount effective to reduce the fertility of that subject. Partial reductions in fertility (i.e., effects which are reflected as a reduction in fertility in a population of subjects) are intended as within the scope of the present invention.

Any animal may be treated by the immunocontraceptive method of the present invention, including both birds and mammals. Exemplary mammals include mice, rabbits, dogs, cats, cows, pigs, sheep, horses, and humans. Mammalian subjects are preferred. The subject may be male or female, but male subjects are preferred. The synthetic peptide may be administered to the subject by any suitable means. Exemplary are by intramuscular injection, by subcutaneous injection, by intravenous injection, by intraperitoneal injection, and by nasal spray.

The amount of synthetic peptide administered will depend upon factors such as route of administration, species, and the use of booster administrations. In general, a dosage of about 0.1 to about 100 μg per pound subject body weight may be used, more particularly about 1 μg per pound.

The immunocontraceptive method of the present invention contemplating both human and veterinary treatments, the synthetic peptides of the present invention may be prepared as both human and veterinary vaccine formulations. Vaccine formulations of the present invention comprise the synthetic peptide in a pharmaceutically acceptable carrier. The synthetic peptide is included in the carrier in an amount effective to reduce the fertility of the subject being treated. Pharmaceutically acceptable carriers are preferably liquid, particularly aqueous, carriers, such as sodium phosphate buffered saline. The vaccine formulation may be stored in a sterile glass container sealed with a rubber stopper through which liquids may be injected and formulations withdrawn by syringe.

Vaccine formulations of the present invention may optionally contain one or more adjuvants. Any suitable adjuvant can be used, exemplary being aluminum hydroxide, aluminuum phosphate, plant and animal oils, and the like, with the amount of adjuvant depending on the nature of the particular adjuvant employed. In addition, the vaccine formulations may also contain one or more stabilizer, exemplary being carbohydrates such as sorbitol, manitol, starch, sucrose, dexrin, and glucose, proteins such as albumin or casein, and buffers such as alkaline metal phosphates and the like.

The diagnostic method of the present invention provides a method of diagnosing autoimmune infertility in both male and female subjects. The term "autoimmune" is here used in a generic sense, as the immunity in female subjects is to exogenous sperm. Currently, we find the diagnostic assay to provide a superior prediction of infertility in male subjects.

Any conventional procedure for detecting serum antibodies can be employed in practicing the diagnostic assay of the present invention, including agglutination and precipitation reactions, radioimmunoassays, enzyme immunoassays (e.g., U.S. Pat. No. 3,654,090) such as Enzyme-Linked Immunosorbent Assays (ELISA), heterogeneous fluorescent immunoassays (e.g., U.S. Pat. Nos. 4,201,763; 4,171,311; and 3,992,631), and homogeneous (separation-free) immunoassays. See generally *Basic and Clinical Immunology,* 364–73 (J. Fudenberg et al eds. 3d Ed. 1980). ELISA is preferred.

In a preferred embodiment, serum from a human to be diagnosed is contacted with an antigen as described above so that antibodies in the serum react in solution with the antigen. The order of addition of these components is not critical. While the antigen is preferably bound to a solid support, if a homogeneous (separation-free) immunoassay is utilized to detect the antibodies, a solid support would not be required.

Serum may be obtained from a person generally by pricking a finger and obtaining whole blood (of which serum is a constituent). However, the blood may be processed to obtain only the serum or plasma portion of the whole blood before contacting the serum with the bound antigens. Any method for obtaining serum or plasma from a patient may be utilized as long as the antibodies contained therein retain their ability to bind the antigen.

The antigens may be bound to solid supports by known techniques. For example, a bi-functional organic molecule may be used to attach the antigen to a solid support. The solid can be made of materials such as plastic (e.g., the bottom surface of a well in a microtiter plate), fiberglass, cellulose acetate and nitrocellulose (e.g., discs). After being attached or adhered to the solid support, the antigens can be cross-linked if desired.

The step of contacting the solid support with a detectable antibody is carried out so that the detectable antibody is allowed to interact with the antigen bound to the solid support. The detectable antibody is one which is capable of binding to a human antibody from the serum of the patient which has bound to the purified antigen, where the detectable antibody is capable of being detected. More particularly, the detectable antibody can be an anti-human immunoglobulin which is conjugated to a group such as an enzyme which is detectable in the presence of a substrate. Enzyme-conjugated goat or rabbit anti-human antibodies which have been affinity purified are preferred. In general, the detectable group which is conjugated to the detectable antibody may be any enzyme or other detectable species which has been developed for immunoassays. For example, enzymes, fluorescent groups, radioactive groups and others could be used. The enzyme peroxidase is particularly preferred. When peroxidase is the detectable group conjugated to the detectable antibody, a substrate such as 3,3′,5,5′-tetramethylbenzidine or o-phenylenediamine may be used as the substrate for detection of the detectable antibody.

The step of detecting the detectable antibody that has reacted with the human antibodies involves treating or manipulating the detectable group which is conjugated to the detectable antibody to determine its presence. For example, if an enzyme such as peroxidase is conjugated to the antibody, the detecting step would involve adding a peroxidase substrate to the bound antibody and observing a color change as peroxidase catalyzes conversion of the substrate to a colored species. In the case of other enzymes, such as alkaline phosphatase and $\beta$-D-galactosidase, other substrates may be used. The substrate to be used should be chosen such that after the enzyme catalyzes a chemical conversion of the substrate to a product, a change which is observable to a person employing this test should result. Substrates such as 3,3′,5,5′-tetramethylbenzidine, p-nitrophenyl phosphate or 3,3′-diamino-benzidine may be used as substrates. Other detectable groups may also be conjugated to the antibody.

A kit containing the required components for carrying out a diagnostic test based on detection of serum antibodies can be assembled. The kit comprises a package containing purified antigen coated in or on a solid support such as the bottom of a microtiter plate well or a nitrocellulose or cellulose acetate disc, and a container of a detectable antibody conjugate which is capable of binding antibody from the serum of a patient which is bound to the antigen. An ELISA test is most preferred for the kit since it lends itself to a readily detectable positive or negative diagnosis. Thus, the kit should also house a container of a substrate which is reactive with an enzyme which is conjugated to the detectable antibody, the substrate being readily detectable after reaction with the enzyme.

The antigen employed in the diagnostic assay is, as noted above, selected from the group consisting of (a) Rabbit Sperm Membrane Autoantigen (RSA), (b) other proteins which bind selection antibodies which bind to RSA, and (c) derivatives of either RSA or these other proteins which bind selection antibodies which bind to RSA. The antigen is preferably substantially free of extraneous proteins. Other proteins which may be employed as antigens are preferably sperm proteins, and more preferably mammalian sperm proteins. Exemplary human sperm proteins which bind selection antibodies which bind to RSA are given in the Examples which follow. A preferred group of selection antibodies are those which bind to the decapeptide $NH_2$-pro-gly-gly-gly-thr-leu-pro-pro-ser-gly-COOH.

Derivatives of RSA and other proteins which bind selection antibodies which bind to RSA have (a) one or more amino acid residues changed, (b) one or more amino acid residues deleted, or (c) one or more amino acid residues changed and one or more amino acid residues deleted. The derivatives are chosen to bind selection antibodies which bind to RSA. Again, a preferred group of selection antibodies are those which bind to the decapeptide $NH_2$-pro-gly-gly-gly-thr-leu-pro-pro-ser-gly-COOH. A preferred group of derivatives is the decapeptide $NH_2$-pro-gly-gly-gly-thr-leu-pro-pro-ser-gly-COOH and the antigenic equivalents thereof, as discussed in detail above.

The examples which follow are provided to illustrate the invention, and are not to be construed as limiting the invention to the specific embodiments described. Temperatures are given in degrees Centigrade unless otherwise indicated.

EXAMPLE 1

Purification of Rabbit Sperm Autoantigen (RSA)

To investigate more precisely the specific epitopes of RSA responsible for its autoantigenicity, we have utilized a kallikrein digest of the isolated 14,000 dalton family member along with peptide sequence analysis and characterization of a synthetic peptide.

RSA was purified from frozen rabbit testes as described previously, M. G. O'Rand and J. P. Porter, 27 *Biol. Reprod.*, 713 (1982). The single 14,000 dalton (14 kd) RSA family member was isolated by excision and electroelution from a slab gel following SDS-PAGE.

EXAMPLE 2

Kallikrein Digestion of Isolated RSA

Approximately 200 ugm of 14 kd RSA, isolated in accordance with Example 1 above, were dialyzed against 6M urea and then against 25 mM Tris-chloride, pH 8.1. Digestion was carried out with 50 ugm of kallikrein (Boehringer-Mannheim, Germany) at 37° C. overnight and then with an additional 20 ugm of kallikrein for four hours. Digests were run on a Dupont peptide reverse phase column (6.2×80 mm) in 0.1% TFA in water with a 0.1% TFA in acetonitrile gradient from 0% to 100% in 65 minutes. Eluted peaks were rerun before sequencing.

Kallikrein digests of 14 kd RSA resulted in several peptide peaks (FIG. 1). Four peaks were selected for analysis (arrows, FIG. 1) and the two major peaks, fractions 19 and 21, were submitted for sequence analysis, as described in Example 3 below.

EXAMPLE 3

Sequencing of Kallikrein Digests and Preparation of Synthetic Autoantigen

Sequencing was carried out by automated Edman degradation on an Applied Biosystems 470A gas phase sequenator having an on-line Applied Systems Model 120A PTH amino acid analyzer. Peptide synthesis was carried out by Peninsula Labs, Belmont, Calif.

Fraction 19 was blocked on the N-terminal and fraction 21 yielded a major and minor sequence. The major consensus sequence from two independent runs was, from N terminal to C terminal: ser-pro-gly-gly-gly-thr-leu pro-pro-ser-gly-gly-trp-trp-ser. From this sequence a ten amino acid peptide designated P10G was synthesized. P10G has the formula $NH_2$-pro-gly-gly-gly-thr-leu-pro-pro-ser-gly-COOH.

EXAMPLE 4

Preparation of Antisera and Affinity-Purified Antibodies to the Synthetic Autoantigen Antisera to RSA was prepared in accordance with known procedures. See, e.g., M. O'Rand, 25 *Biol. Reprod.*, 611 (1981); M. G. O'Rand, G. P. Irons and J. P. Porter, 30 *Biol. Reprod.* 721 (1984). Antisera to the synthetic autoantigen was prepared in the same manner, except that the peptide (ten mgm) was conjugated to thyroglobulin and then used for immunization. The serum was subsequently affinity purified by passing it over an agarose column (Reacti-gel 6x, Pierce Chemical Co.) coupled with the synthetic peptide P10G.

EXAMPLE 5

ELISA Procedures

ELISA was carried out in accordance with known procedures. See, e.g., M. O'Rand et al., 129 *Dev. Biol.* 231 (1988). In brief, 1 microgram of the decapeptide described in Example 3 above was fixed to the bottom surface of wells in 96 well microtiter plates by cross linking with Bouin's fixative in accordance with known techniques. See. e.g., W. Noteboom et al., 75 *J. Immunol. Methods* 141 (1984). Peroxidase-labelled goat anti-rabbit and anti-human IgG was used as the detectable antibody and 3,3',5,5'-Tetramethylbenzidine (TMB) was used as the substrate. The TMB reaction product was read as a yellow product after the addition of 1 Normal HCl.

EXAMPLE 6

Cross-Reactivity of RSA and Synthetic Autoantigen

Figure 2:
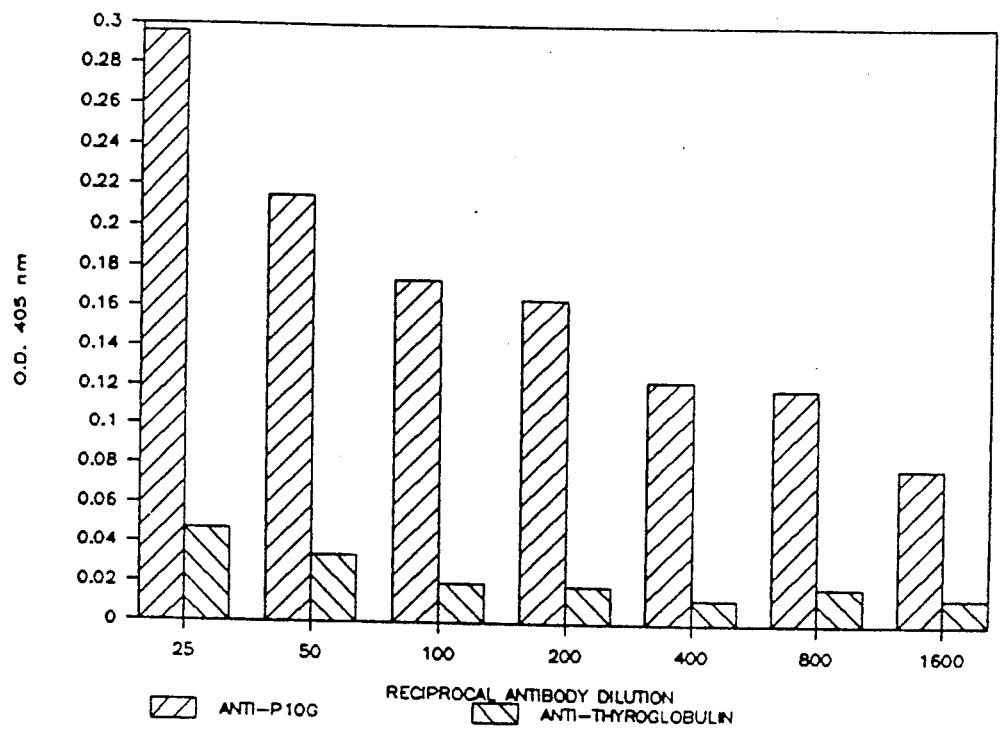
FIG. 2 shows the ELISA of affinity purified anti-P10G antibodies reacted with RSA. Anti-thyroglobulin is the control antiserum.
Figure 3:
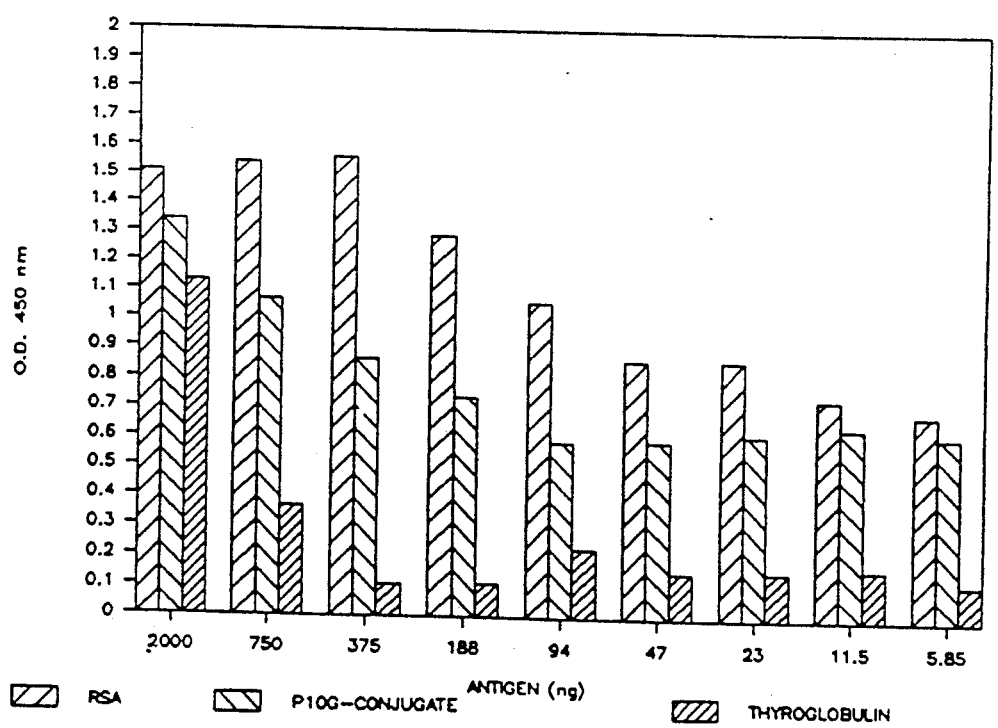
FIG. 3 shows the ELISA of anti-RSA antiserum reacted with RSA, P10G-conjugate and thyroglobulin.
Figure 4:
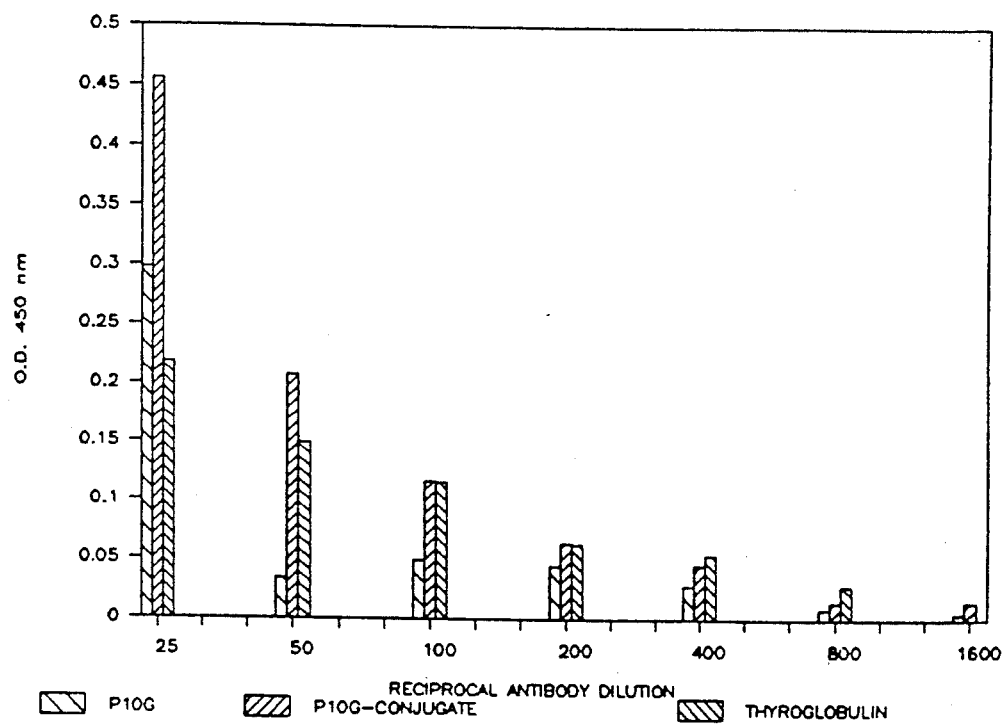
FIG. 4 shows the ELISA of rabbit anti-rabbit sperm autoantiserum reacted with P10G, P10G-conjugate and thyroglobulin.

Affinity purified anti-P10G antibodies reacted with RSA in ELISA (FIG. 2) in greater than a 1:1600 dilution. ELISA was carried out according to the procedures described in Example 5 above. Control anti-thyroglobulin antibodies showed only minimal reactivity to RSA (FIG. 2). Similarly, anti-RSA antibodies reacted in ELISA with as little as 5.85 ngm of P10G-conjugate or RSA while only reacting minimally to thyroglobulin control (FIG. 3). Rabbit anti-rabbit sperm autoantiserum reacted with both P10G and P10G-conjugate in ELISA, indicating that P10G is an autoantigenic epitope (FIG. 4). The autoantiserum also reacted with thyroglobulin, but to a lesser degree than with P10G-conjugate (FIG. 4). Additionally, affinity purified anti-P10G antibodies reacted with the 14 kd RSA band on Western blots and showed strong equatorial fluorescence on acrosome intact ejaculated rabbit spermatozoa using indirect immunofluorescence.

EXAMPLE 7

Reactivity of Anti-RSA Antisera With Human Spermatazoa Proteins

Western blots of SDS-PAGE of human (lanes 1,4,7), pig (lanes 2,5,8) and rabbit (lanes 3,6,9) sperm lysates were conducted. 200 μg of protein were loaded in each lane. Lanes 1,2,3 were stained with amido black; lanes 4,5,6 were control lanes stained with biotin labeled goat anti-mouse immunoglobulin (A, G and M, heavy chain specific) (GAM-b), followed by avidin-alkaline phosphatase (AAP) and NBT/BCIP substrate; lanes 7,8,9 were stained with mouse anti-RSA, GAM-b, AAP and NBT/BCIP. Immunologically cross-reactive RSA-like molecules of 65-70 kD in were found in human (lane 7) and pig (lane 8) spermatozoa. The major bands were at 70 kD and 65 kD. These bands represent aggregated forms of RSA. O'Rand et al., 129 *Dev. Biol.* 231 (1988). Control blots with only second antibody (goat anti-mouse, lanes 4,5,6) were negative.

For comparison, western blots of SDS-PAGE of purified RSA, lanes 1,3,5 (43 μg protein loaded in each lane) and rabbit sperm lysate, lanes 2,4,6 (200 μg protein loaded in each lane) were conducted. Lanes 1 and 2 were control lanes; lanes 3 and 4 were mouse anti-RSA lanes; lanes 5 and 6 were amido black lanes. Blots were stained as described above, and the same antisera as used above was used. In this case, the antisera detects one of the lower molecular forms (16 kD) and the aggregated forms (65-70 kD) on the blot (lane 3). In rabbit spermatozoa (lane 4) the antiserum detects the aggregate forms.

Figure 5:
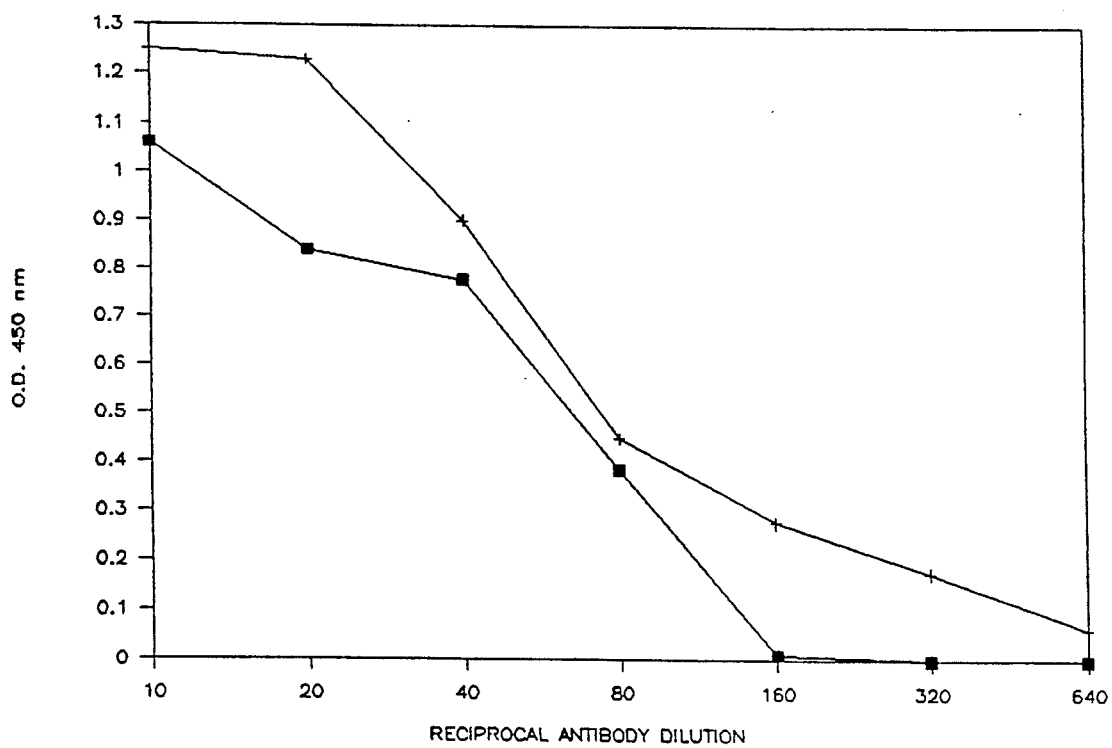
FIG. 5. ELISA of mouse anti-RSA (+) and affinity purified rabbit anti-P10G (•) on human sperm lysate. Control values for preimmune sera were subtracted from the ELISA values at each dilution. Each point is the mean of a triplicate determination.

The reactivity of anti-RSA antisera with human spermatozoa can also be demonstrated by ELISA (FIG. 5). ELISA methods were carried out in accordance with known techniques. See e.g., O'Rand et al., 129 *Dev. Biol.* 231 (1988). FIG. 5 shows that anti-RSA antiserum has a significant titer (≦1/640) against human sperm lysate. Since P10G is an epitope within RSA, it would be expected that antibodies to P10G would also react against human spermatozoa. FIG. 5 also shows the reactivity of affinity purified anti-P10G antibodies on human sperm lysate.

The immunofluorescent localization of anti-RSA antisera on human spermatozoa was also examined. Immunofluorescent and labeling methods were carried out in accordance with known techniques. See, e.g., N. Esaguy et al., 19 *Gamete Res.* 387 (1988). Fluorescence was seen localized around the entire head plasma membrane and may on some sperm be concentrated in the post-acrosomal and neck regions. Spermatozoa treated with adjuvant control sera stained only very weakly. Matched phase contrast images showed localizations similar to those seen on rabbit spermatozoa. See N. Esaguy et al., supra, M. O'Rand and L. Romrell, 84 *Dev. Biol.* 322 (1981).

EXAMPLE 8

Reactivity of Antisera from Infertile Men With Synthetic Autoantigen

Figure 6:
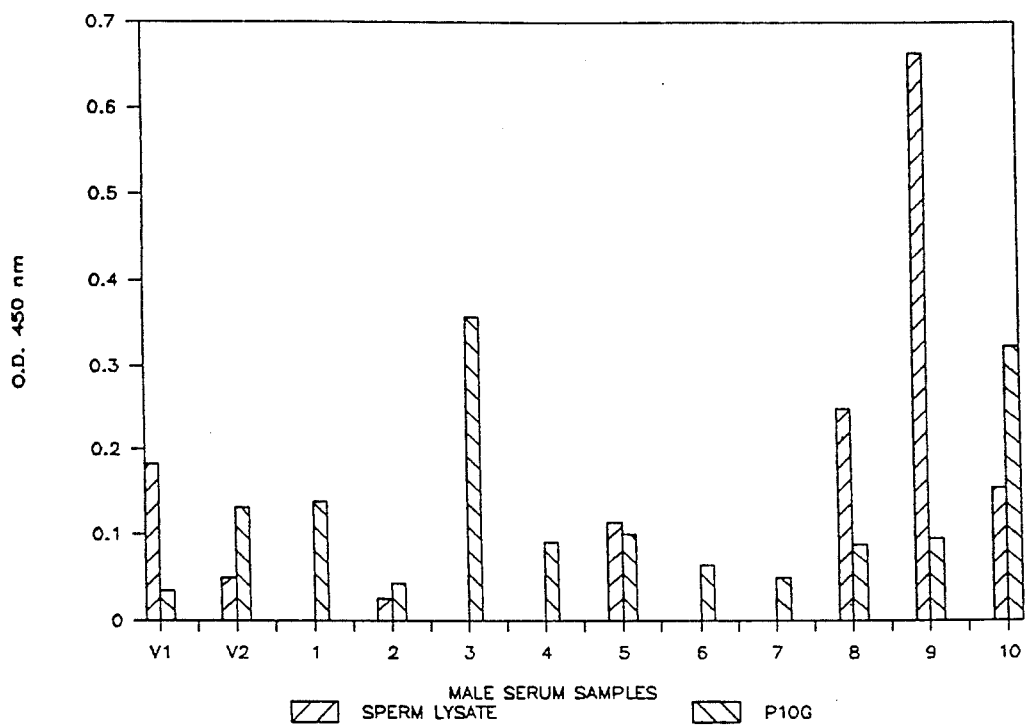
FIG. 6. ELISA of sera from vasectomized (V1, V2) and infertile males (#1-#10) on P10G [\\\] and human sperm lysate [///].

Because the synthetic autoantigen (P10G) prepared in Example 3 above is an autoantigenic epitope, antisera from vasectomized men as well as sera from men attending an infertility clinic were tested for reactivity to P10G. FIG. 6 shows the results of an ELISA on two samples from vasectomized men (V1 and V2) and ten different sera from male patients attending an infertility clinic. ELISA was carried out in accordance with the procedures given in Example 5. Reactivity to human sperm lysate is also shown for comparison. In both vasectomized sera antibodies to P10G can be detected and in every case where anti-sperm antibodies are seen, the sera is also positive for P10G. Infertile sera without strong anti-sperm antibody activity is also positive. The mean ELISA value for reactivity to P10G (0.01625±0.0234 S.D.) is based on 4 sera of normal fertile females who were negative in the anti-sperm antibody bead test. R. Bronson et al., 8 *J. Reprod. Immunol.* 279 (1985). Of the ten male samples, seven were more than two standard deviations (±0.0468) above the mean ELISA value (0.01625) of reactivity to P10G. The anti-sperm antibody ELISA values have had the mean ELISA value of the 4 normal sera (negative bead test) subtracted from them.

EXAMPLE 9

Reactivity of Antisera from Infertile Women With Synthetic Autoantigen

Figure 7:
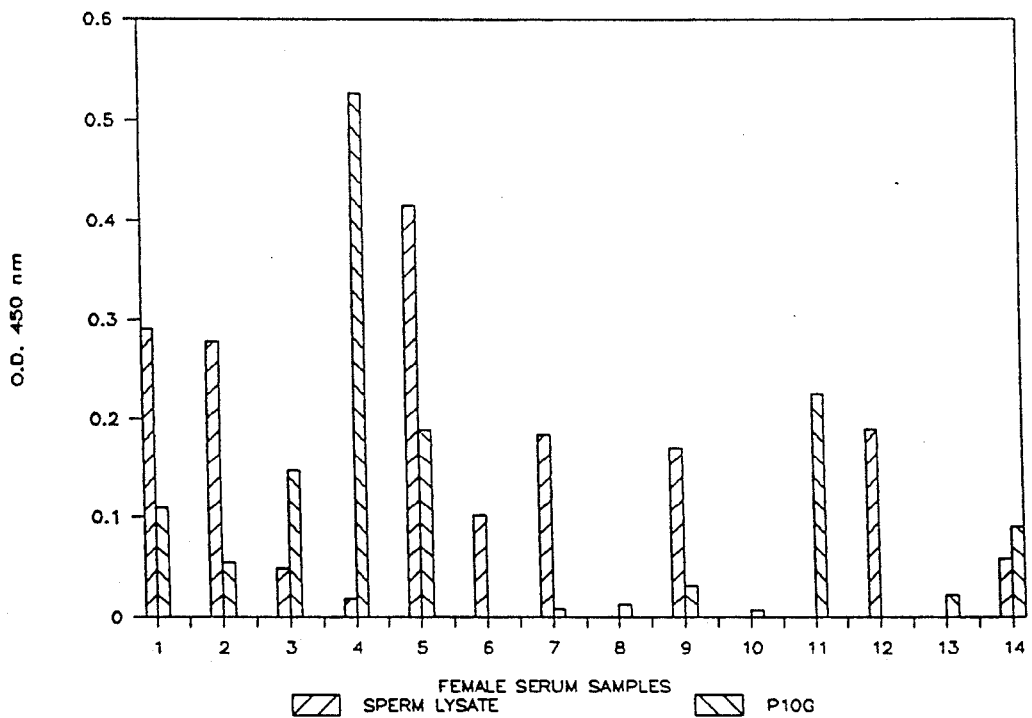
FIG. 7. ELISA of sera from infertile females (#1-#14) on P10G [\\\] and human sperm lysate [///].

FIG. 7 shows the results of an ELISA on fourteen different sera from female infertility patients. ELISA was carried out in accordance with the procedures given in Example 5. Two of the fourteen (#6 and #12) had anti-sperm antibodies but did not react with P10G. Of the fourteen sera, six were more than two standard deviations (±0.0468) above the mean ELISA value (0.01625) of reactivity to P10G. The mean P10G ELISA value is the same as used in FIG. 6. The anti-sperm antibody ELISA values have been corrected as in FIG. 6.

The foregoing Examples are illustrative of the present invention, and are not to be taken as limiting thereof. The invention is defined by the following claims, with equivalents of the claims to be included therein.

That which is claimed is:

1. A synthetic peptide, useful as an immunocontraceptive agent and for the diagnosis of autoimmune infertility, selected from the group consisting of the decapeptide $NH_2$-pro-gly-gly-gly-thr-leu-pro-pro-ser-gly-COOH and the antigenic equivalents thereof, said antigenic equivalents being:
   (a) a modified decapeptide comprising said decapeptide modified by replacing of one or more amino acids to the sequence thereof; or
   (b) a longer peptide which incorporates the sequence of said decapeptide or said modified decapeptide and which has (i) up to four extra amino acid residues attached to the C-terminal end of said sequence, (ii) up to four extra amino acid residues attached to the N-terminal end of said sequence, or (iii) up to four extra amino acid residues attached to the C-terminal end of said sequence and up to four extra amino acid residues attached to the N-terminal end of said sequence;

wherein said antigenic equivalents bind to antibodies which bind to the decapeptide $NH_2$-pro-gly-gly-gly-thr-leu-pro-pro-ser-gly-COOH.

2. A synthetic peptide according to claim 1 including the sequence, from the N terminal to C terminal thereof, of -ser-pro-gly-gly-gly-thr-leu-pro-pro-ser-gly-gly-trp-trp-ser-.

3. A synthetic peptide according to claim 1 including the sequence, from N terminal to C terminal thereof, of -pro-gly-gly-gly-thr-leu-pro-pro-ser-gly-.

4. A synthetic peptide according to claim 1 having the formula $NH_2$-ser-pro-gly-gly-gly-thr-leu-pro-pro-ser-gly-gly-trp-trp-ser-COOH.

5. A synthetic peptide according to claim 1 having the formula $NH_2$-pro-gly-gly-gly-thr-leu-pro-pro-ser-gly-COOH.

6. An immunocontraceptive method comprising administering to an animal subject a synthetic peptide according to claim 1 in an amount effective to reduce the fertility of said subject.

7. An immunocontraceptive method according to claim 6, wherein said subject is a mammalian subject.

8. An immunocontraceptive method according to claim 6, wherein said subject is a male subject.

9. An immunocontraceptive vaccine formulation comprising a synthetic peptide according to claim 1 in an amount effective to reduce the fertility of an animal subject in combination with a pharmaceutically acceptable carrier.

10. An immunocontraceptive vaccine formulation as claimed in claim 9, further comprising an adjuvant.

11. An immunocontraceptive vaccine formulation as claimed in claim 9, further comprising a stabilizer.

12. A kit comprising the synthetic peptide of claim 1.

13. A method of diagnosing autoimmune infertility in a human subject comprising:
   (a) collecting an immune sera sample from the subject, and then
   (b) detecting the presence of antibodies from the immune sera sample which bind to Rabbit Sperm Membrane Autoantigen, the presence of said antibodies suggesting the subject is afflicted with autoimmune infertility.

14. A diagnostic method according to claim 13, wherein said subject is a male subject.

* * * * *